United States Patent [19]

Lieberman

[11] Patent Number: 4,627,433
[45] Date of Patent: Dec. 9, 1986

[54] TRACHEOSTOMY DEVICE

[76] Inventor: Edgar M. Lieberman, 210 Westport Rd., Kansas City, Mo. 64111

[21] Appl. No.: 835,760

[22] Filed: Mar. 3, 1986

Related U.S. Application Data

[62] Division of Ser. No. 674,243, Nov. 23, 1984, Pat. No. 4,596,248.

[51] Int. Cl.$^4$ ............................................. A61M 16/00
[52] U.S. Cl. ................................................. 128/207.16
[58] Field of Search ..................... 128/207.16; 623/9

[56] References Cited

U.S. PATENT DOCUMENTS

| | | | |
|---|---|---|---|
| 1,835,757 | 12/1931 | Burchett | 128/207.17 |
| 2,804,076 | 8/1957 | Giraudon | 128/207.16 |
| 3,066,674 | 12/1962 | Capra | 128/207.16 |
| 3,263,684 | 8/1966 | Bolton | 128/207.16 |
| 3,504,676 | 4/1970 | Lomholt | 128/207.15 |
| 3,529,596 | 9/1970 | Garner | 128/207.15 |
| 3,659,612 | 5/1972 | Shiley et al. | 128/207.15 |
| 3,683,931 | 8/1972 | Chelucci et al. | 128/207.16 |
| 3,693,624 | 9/1972 | Shiley et al. | 128/207.15 |
| 3,924,637 | 12/1975 | Swanson | 128/207.16 |
| 3,952,335 | 4/1976 | Sorce et al. | 128/207.16 |
| 4,009,720 | 5/1977 | Crandall | 128/207.15 |
| 4,037,605 | 6/1977 | Firth | 128/207.15 |
| 4,040,428 | 8/1977 | Clifford | 128/207.16 |
| 4,223,411 | 9/1980 | Schoendorfer et al. | 128/207.16 |
| 4,280,492 | 7/1981 | Latham | 128/207.16 |
| 4,325,366 | 4/1982 | Tabor | 128/207.16 |
| 4,449,523 | 5/1984 | Szachowicz et al. | 128/207.15 |
| 4,459,984 | 7/1984 | Liegner | 128/207.16 |

OTHER PUBLICATIONS

Safar et al., "Speaking Cuffed Tracheostomy Tube", Critical Care Medicine, vol. 3, No. 1, Jan.-Feb. 1975, pp. 23-26.
Shiley brochure, "Disposable Cannula Tracheostomy Tube", Apr. 1982.
Maisel, et al., "The Communitrach I: Use in the Vocal and Non-Vocal Patient"; presented at the Fifth Asia-Oceania Congress of Otorhinolaryngological Societies, Seoul, Korea, Oct. 9-14, 1983.
Szachowicz et al., "A Modified Tracheostomy Tube Which Allows Normal Laryngeal Speech While on a Ventilator" (preprint), Scientific Paper for Publication in Surgical Forum, & for presentation at The Clinical Congress of American College of Surgeons, Atlanta, Oct. 1983.

Primary Examiner—Kyle L. Howell
Assistant Examiner—Ruth S. Smith
Attorney, Agent, or Firm—Litman, Day & McMahon

[57] ABSTRACT

A tracheostomy device for insertion into the trachea for ventilation has inner and outer cannulae. A sealing cuff on the inner cannula forms a seal with a wall of the trachea. A housing connects to the inner and outer cannulae and communicates with an outside air source. The outer cannula is provided with a fenestration between the cuff and the patient's vocal cords. The inner cannula is slidable within the outer cannula, the two being connected by a spring and bellows arrangement. The inner cannula slides down to close the fenestration during inhalation and slides up to open the fenestration upon exhalation of the air from the patient's lungs.

2 Claims, 14 Drawing Figures

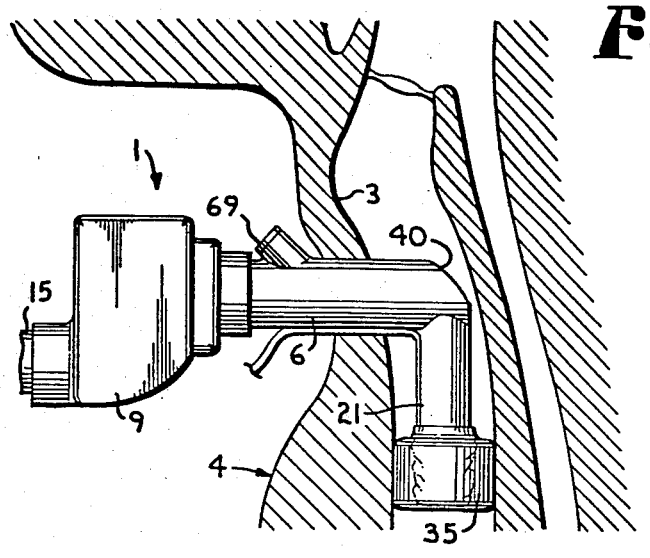
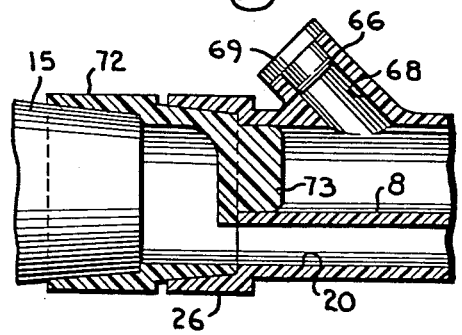
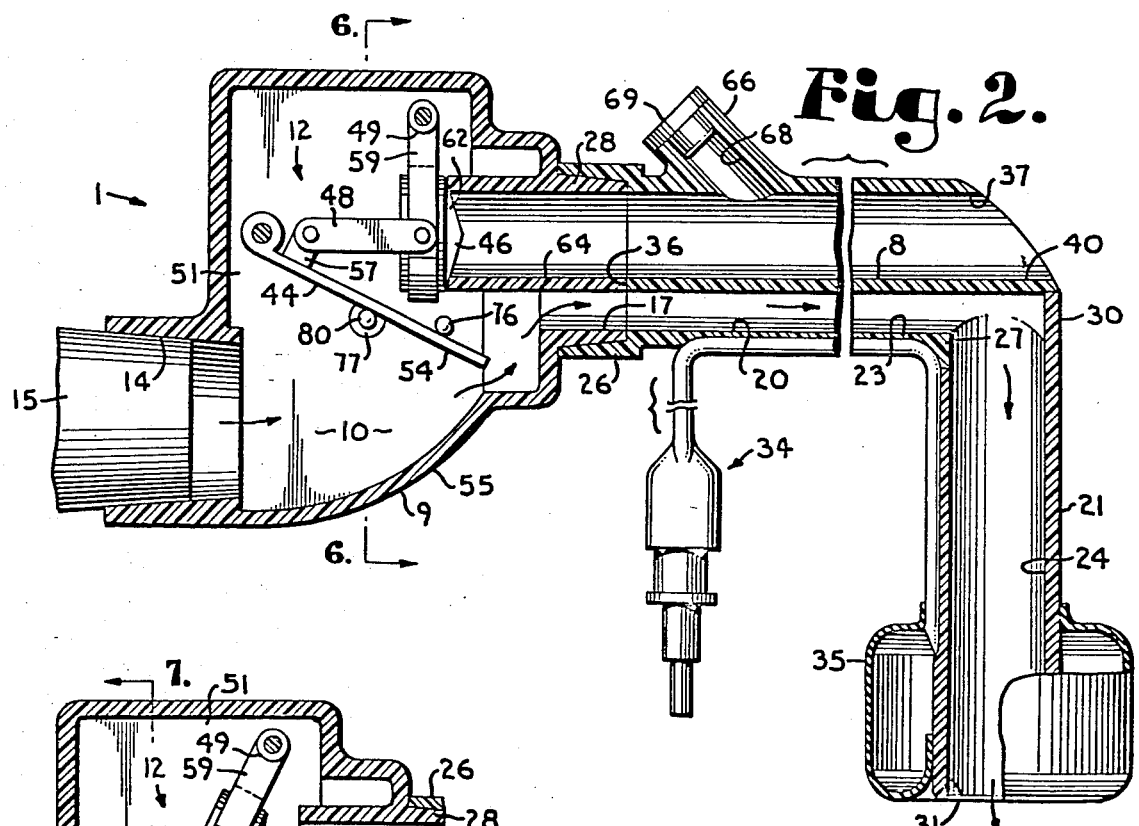
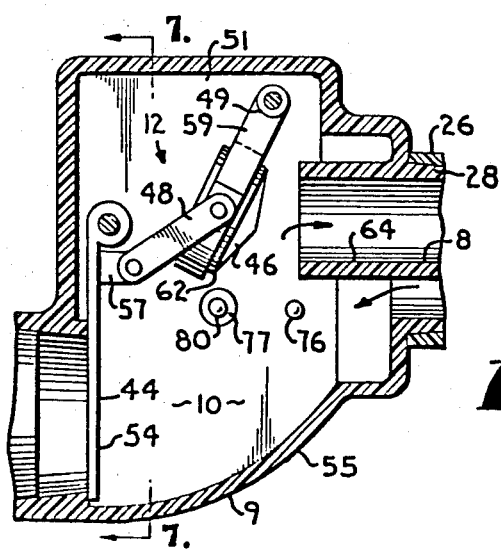

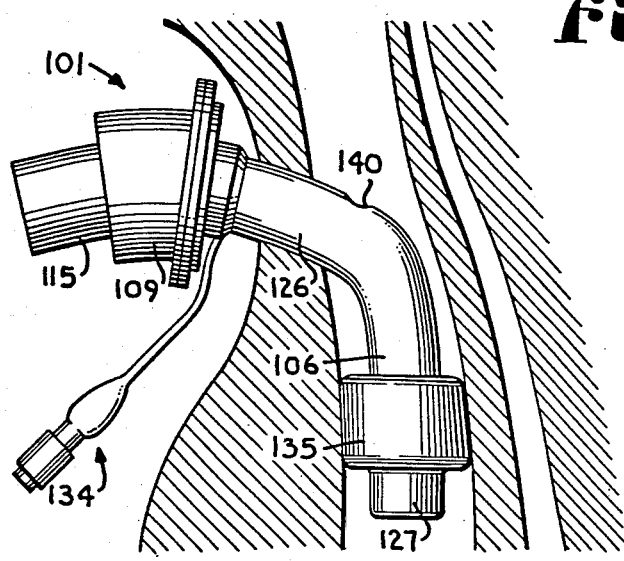
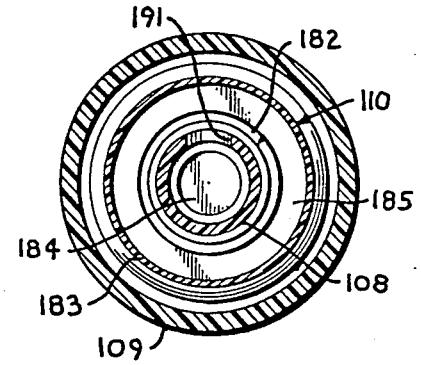
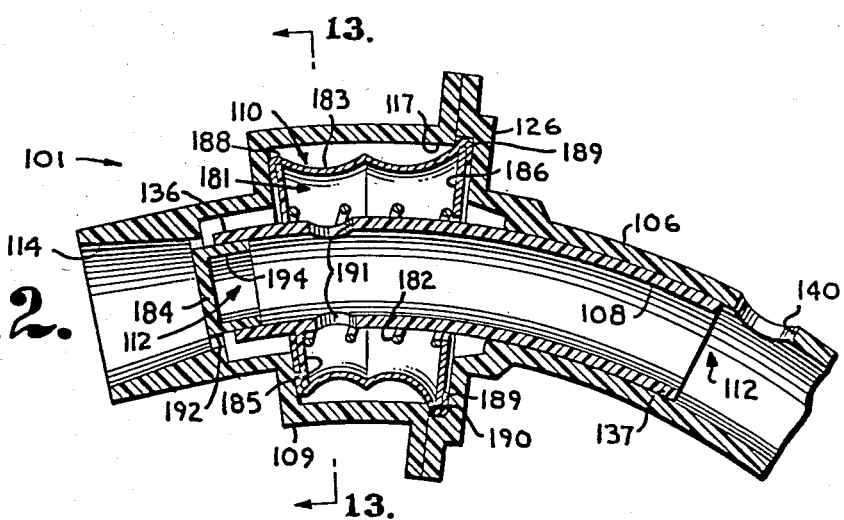
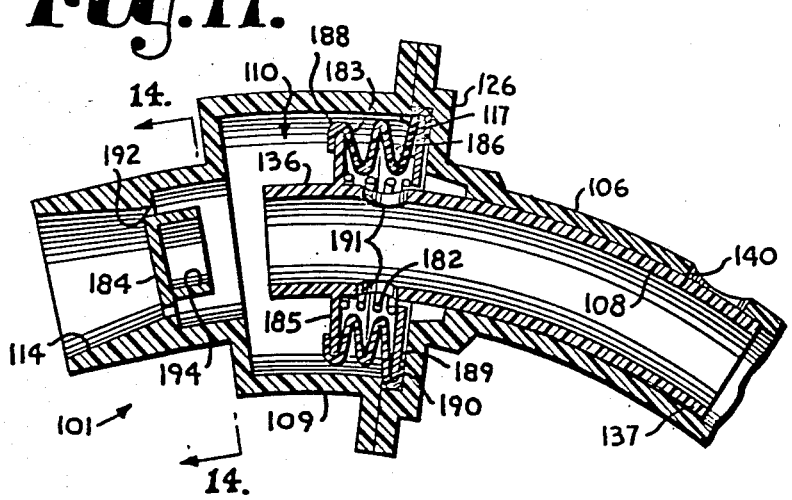
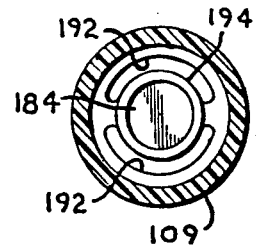

TRACHEOSTOMY DEVICE

CROSS-REFERENCE TO RELATED APPLICATION

The present application is a division of U.S. application for patent, Ser. No. 674,243, filed Nov. 23, 1984, now U.S. Pat. No. 4,596,248.

BACKGROUND OF THE INVENTION

The present invention relates to tracheostomy devices and particularly to such tracheostomy devices for allowing a patient to speak during forced ventilation and natural breathing.

Under certain conditions, a medical patient who is having difficulty breathing will undergo a tracheotomy operation. During this operation, an incision is made to establish air communication with the interior of the patient's trachea. A tracheostomy device is inserted through the incision into the trachea. Typically, air is forced through the trachea and into the patient's lungs to assist in breathing.

Many tracheostomy devices are provided with a circumferential cuff which seals a lower portion of the trachea and the lungs from the patient's upper airway. In doing this, the exhaled air is forced out through the tracheostomy device, and is not allowed to pass over the patient's vocal cords, thus preventing the patient from speaking. With select patients, the inability to speak can be a major inconvenience, and conceivably a dangerous situation if the person cannot otherwise communicate.

Several attempts have been made to provide air to the upper trachea airway to allow vocalization. However, many of the prior devices have forced outside air into the upper trachea airway. Such devices are difficult to work, are uncomfortable and the resulting speech is muffled and barely understandable. Attempts have also been made to direct the patient's own exhaled air into the upper trachea airway, but these have either required the absence of the sealing cuff or have been found to be complex and cumbersome to use and are susceptible to clogging.

The sealing cuff is important for preventing foreign material from entering the lungs.

OBJECTS OF THE INVENTION

The principal objects of the present invention are: to provide a cuffed speaking tracheostomy device for protection of the lungs and forced or natural respiration of a patient while allowing the patient to speak; to provide such a tracheostomy device which comprises a dual valve system for regulating flow of air into and out of the lungs and larynx; to provide such a tracheostomy device having the dual valve system which is highly responsive to relatively low pressures that are present in the respiration process; to provide such a tracheostomy device which permits a patient to speak using the patient's own exhalation air; to provide such a device for measuring the exhalation volume of the patient when desired; to provide such a tracheostomy device having a dual valve system which is responsive to a patient's exhaled breath; to provide such a tracheostomy device having a dual valve means including a spring and bellows arrangement and slidable inner cannula for opening and closing a fenestration in an outer cannula; to provide such a tracheostomy device which is highly reliable in use and is removable for cleaning; to provide such a tracheostomy device which is automatically responsive to a patient's natural respiration process and is workable in substantially any position; to provide such a tracheostomy device which is relatively simple to use, economical to manufacture and particularly well adapted for the proposed usage thereof.

Other objects and advantages of this invention will become apparent from the following description taken in conjunction with the accompanying drawings wherein are set forth, by way of illustration and example, certain embodiments of this invention.

SUMMARY OF THE INVENTION

A cuffed speaking tracheostomy device is provided for permitting a patient to speak during forced and natural ventilation using his or her own exhaled air. The tracheostomy device is adapted for insertion into the trachea and has first and second cannulae.

A sealing cuff is provided on the first cannula to form a seal with a wall of the trachea. The first cannula is open to the trachea at a location between the sealing cuff and the patient's lungs, and the second cannula is open to the trachea at a position between the cuff and the patient's larynx.

A housing is connected to the first and second cannulae and provides selective air communication with an outside air source. The housing contains a dual valve system including a swingable check valve connected by a toggle link to a swingable plug valve. The check valve selectively opens and closes a housing aperture to regulate flow of air from the air source. The plug valve moves in conjunction with the check valve and selectively seals the second cannula to regulate flow of air through the second cannula and to an upper portion of the trachea.

The check valve and plug valve move together from a first position in which the check valve is open to allow air to flow from the air source and through the housing and the first cannula to a lower portion of the trachea and the lungs and the plug valve seals the second cannula. A second position results upon exhalation of the air from the patient's lungs whereby the exhaled air moves the check valve from the first position into contact with the housing to seal the housing aperture. The plug valve is simultaneously moved away from the second cannula, forcing air to flow through the second cannula into the upper portion of the trachea, thereby allowing the patient to speak by means of his or her own exhaled air.

Alternatively, the outer cannula is provided with a fenestration between the cuff and the patient's vocal cords. The inner cannula is slidable within the outer cannula by means of a spring and bellows arrangement. The inner cannula slides down to close the fenestration during inhalation and slides up to open the fenestration upon exhalation of the air from the patient's lungs.

Means are provided to lock the plug valve and the check valve in position so that the exhaled air is directed back toward the air source. This is necessary so that the patient's breathing can be monitored.

The drawings constitute a part of this specification and include exemplary embodiments of the present invention and illustrate various objects and features thereof.

BRIEF DESCRIPTION OF THE DRAWINGS

FIG. 1 is a fragmentary side elevational view of a tracheostomy device embodying the present invention shown in an operative position within a patient's trachea.

FIG. 2 is an enlarged, fragmentary side elevational view of the tracheostomy device, with portions broken away and showing dual valve means in a first position.

FIG. 3 is an enlarged, fragmentary side elevational view of the tracheostomy device with portions broken away and showing the dual valve means in a second position.

FIG. 9 is a fragmentary, longitudinal section view of a ventilation connector fitted into first and second cannulae of the present invention.

FIG. 10 is a side elevational view of a modified tracheostomy device according to the present invention.

FIG. 11 is an enlarged, longitudinal section view of the modified tracheostomy device showing a spring and bellows arrangement and inner cannula in a first position.

FIG. 12 is an enlarged, longitudinal section view of the modified tracheostomy device showing the spring and bellows arrangement and inner cannula in a second position.

FIG. 13 is an enlarged, cross-sectional view of the modified tracheostomy device taken along line 13—13, FIG. 12.

FIG. 14 is an enlarged, cross-sectional view taken along line 14—14, FIG. 11.

DETAILED DESCRIPTION OF THE INVENTION

Figure 4:
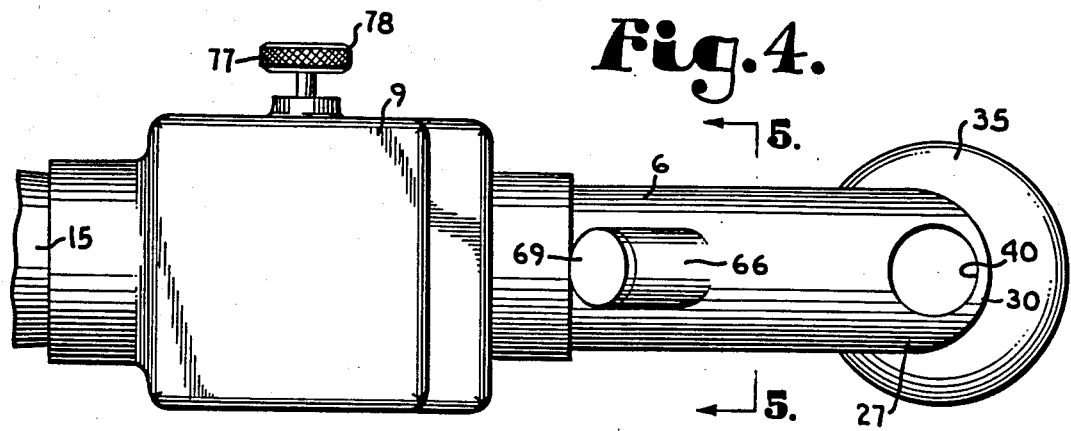
FIG. 4 is an enlarged, top plan view of the tracheostomy device as it is oriented in FIG. 1.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally indicates a tracheostomy device embodying the present invention. As seen in FIG. 1, the tracheostomy device 1 is adapted to be inserted into a trachea 3 of a human patient 4. The tracheostomy device 1 includes a first cannula 6, a second cannula 8 and a dual valve housing 9. Contained within a chamber 10 of the housing 9 are dual valve means 12.

The housing 9 has a first housing aperture 14 therein, which is adapted to receive a ventilation connector 15 from a pressurized air source (not shown). A second housing aperture 17 is generally oppositely positioned relative to the first housing aperture 14. If the patient can breathe on his or her own, the air source is not connected, and the patient simply uses the device 1 to breathe ambient air.

The air source is typically a forced-air respirator as is well known in the art. The respirator is equipped to regulate flow of air so as to pulsate air into the tracheostomy device, in simulation of a person's inhalation. Upon delivering a pulse, the respirator "relaxes" and does not provide a continuous flow of air. The timing of the air pulsations is controlled by a health professional. The respirator is adapted to receive an exhaled breath from the patient during the relaxation phase and to observe the breath by measuring flow rate, volume and the like.

As illustrated, the first cannula 6 has an upper section 20 and a lower section 21. The first cannula upper and lower sections 20 and 21 define respective upper and lower passages 23 and 24. The first cannula upper section has a first end 26 and a second end 27. The first upper section first end 26 is adapted to receive a connector portion 28 of said housing 9.

The first cannula lower section has a first end 30 and a second end 31. As illustrated, the second end 27 of the first cannula upper section 20 is connected to the first end 30 of the first cannula lower section 21 such that the first cannula upper and lower passages 23 and 24 are in air communication with each other. The first cannula upper and lower sections 20 and 21 are disposed generally at right angles to one another, but it is envisioned that this angular disposition can be varied without affecting the present invention.

Inflatable sealing means are included, such as a sealing cuff 35. The cuff 35 is shown in a deflated condition in FIG. 1 as indicated by the phantom lines. With further reference to FIG. 1, the sealing cuff 35 surrounds the second end 31 of the first cannula lower section 21. When inflated, the sealing cuff 35 contacts the trachea and seals the lower portion of the trachea from contamination by foreign material. The first cannula lower passage 24 opens into a lower airway of the trachea below the cuff, that is, between the cuff 35 and the patient's lungs. The inflatable sealing means further include appropriate inflation means 34, as are well known in the art.

The second cannula 8 is shown as an inner cannula or conduit within the first, or outer, cannula 6. It is envisioned, however, that the present invention could be fabricated such that the second cannula 8 and first cannula 6 are located adjacent one another, but not one within the other. Further, the first and second cannulae 6 and 8 can be formed as a single, split tube with adjacent conduits separated by an interior wall.

Figure 5:
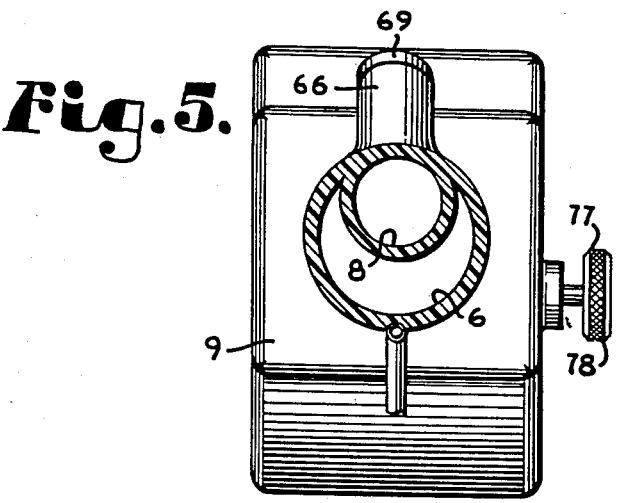
FIG. 5 is an enlarged, cross-sectional view of the tracheostomy device taken along line 5—5, FIG. 4.

The second or inner cannula 8 has a first end 36 and a second end 37. As seen in FIG. 5, the first and second cannulae 6 and 8 may be formed, as out of polyvinylchloride, to have a common wall therebetween.

The second cannula second end 37 extends through a wall of the second end 27 of the first cannula upper section 20, defining an opening or fenestration 40 therethrough. The second cannula 8 is a conduit for exhalation air from the patient's lungs and the fenestration 40 opens into an upper airway of the trachea at a location above the cuff, that is, between the cuff 35 and the patient's larynx.

The dual valve means 12 includes a first or check valve 44, a second or plug valve 46, a toggle link 48 and a guide link 49.

The check valve 44 is swingably connected to opposite side walls 51 and 52 of the housing 9. As shown, the check valve 44 has a generally rectangular flapper plate 54, which corresponds generally in shape to the housing walls. A housing end wall 55 is curved to generally correspond to an arc of swing of the check valve 44.

Figure 6:
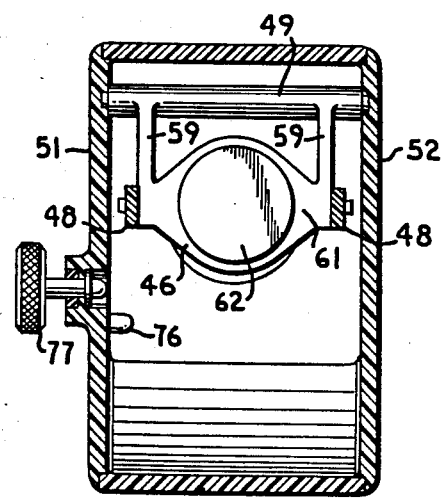
FIG. 6 is an enlarged, cross-sectional view of the tracheostomy device taken along line 6—6, FIG. 2.
Figure 7:
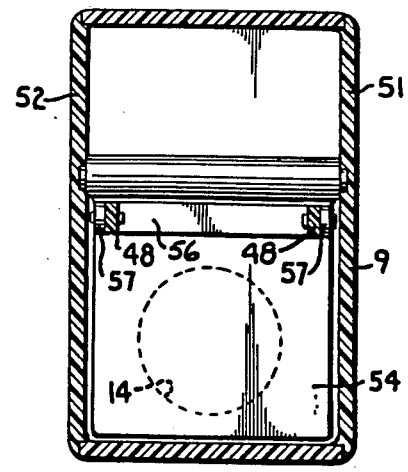
FIG. 7 is an enlarged, cross-sectional view of the tracheostomy device taken along line 7—7, FIG. 3.

The check valve 44 has a yoke 56 with a projecting tab 57, which is connected to one end of the toggle link 48, as seen in FIGS. 6 and 7. An opposite end of the toggle link 48 is swingably connected to an arm 59 of the guide link 49. As shown, a pair of tabs 57, toggle link 48 and arm 59 are provided. The guide link 49 is swingably connected to the housing side walls 51 and 52, as illustrated in FIG. 6. The plug valve 46 comprises a base 61, which is shown as being integral with the guide link arms 59. The plug valve 46 further comprises a sealing member 62, which closes the second cannula 8. The low resistance to free movement of the check valve 44, while providing closure of the plug valve 46, is a result of the mechanical advantage due to the placement and configuration of the toggle link 48.

The check valve 44 and plug valve 46 are connected by the toggle link 48 so that a movement of the check valve 44 initiates a corresponding movement of the plug valve 46, as detailed below.

As seen in FIG. 2, the housing 9 includes a second cannula extension member 64. The extension member 64 extends the cannula 8 and is contacted by the plug valve 46. Although the extension member 64 is shown in the illustrated embodiment, it is envisioned that the second cannula 8 could extend into the housing chamber 10 to be in a position to contact the plug valve 46.

A suction member 66 extends from the integral wall of the first and second cannulae 6 and 8, as best illustrated in FIGS. 2, 4 and 5. The suction member 66 has a suction passage 68 in air communication with the second cannula 8. An appropriate suction plug 69 is provided to close the passage 68 when not in use. The suction passage 68 provides access to the second cannula 8 and to the trachea 3 above the cuff 35. Upon removal of the suction plug 69, a catheter (not shown) can be inserted through the suction passage 68 and the second cannula 8, whereby mucous and the like can be removed from the trachea 3 to keep the fenestration 40 and second cannula 8 clear of obstruction.

As illustrated in FIG. 9, a ventilation adaptor 72 may be substituted for the housing 9 when the housing 9 and dual valving means 12 are periodically removed for cleaning. In that event, provision is made to continue respiration either by force or naturally. The ventilation adaptor 72 fits into the first end 26 of the first cannula upper section 20, and is formed to receive the air source connector 15. Inasmuch as the dual valve means 12 has been removed, the second cannula 8 must be closed to any flow of air, thus allowing monitoring of the patient's exhalation. Accordingly, the ventilation adaptor 72 includes a stopper portion 73 which fits into the second cannula 8, for the above purpose.

Figure 8:
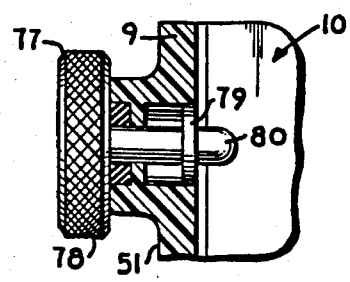
FIG. 8 is an enlarged, fragmentary side view of a locking pin of the present invention.

A stop pin 76 is included to limit the swinging movement of the check valve 44. A movable retaining pin 77, as detailed in FIG. 8, includes a head 78, which extends through a rubber grommet 79 in the housing 9, and a projection 80. When in the position shown in FIG. 8, the projection 80 serves to lock the check valve 44 in place in the position shown in FIG. 2 so the exhalation volume of the patient can be monitored.

In use, the various elements of the dual valve means 12 are adapted to respond to very low pressure differentials, such as are present when a person breathes.

FIG. 2 illustrates a first position of the valve means 12, in which an air pulse is flowing from the air source through the first housing aperture 14 and into the chamber 10. The air pulse acts against the check valve 44, specifically the flapper plate 54, swinging same through its arc away from the first housing aperture 14. The check valve 44 is stopped from further swinging by the stop pin 76.

This movement of the check valve 44 actuates the toggle link 48 to move the plug valve 46 into a seated position against the second cannula extension member 64 (or the second cannula 8, as discussed above). The guide link 49 positions the plug valve 46 to properly contact the second cannula extension member 64. In the first position, air flows through the chamber 10, past the check valve 44, through the first cannula upper and lower passages 23 and 24 and into the trachea 3 for presentation to the patient's lungs. In the first position, the plug valve 46 is sealed against the second cannula extension member 64, and air is prevented from flowing through the second cannula 8.

FIG. 3 shows a second position of the valve means 12, which results from natural exhalation of air from the patient's lungs. As the air is exhaled from the lungs, it travels back through the first cannula lower passage 24 into the upper passage 23 and acts against the check valve 44, specifically the flapper plate 54. This force, albeit small, is sufficient to move the check valve 44 from the first position to the second position, due mainly to the long lever arm and relatively large surface area subject to the differential pressure during respiration. In the second position, the flapper plate 54 contacts the housing 9, and seals the first housing aperture 14.

This movement of the check valve 44 swings the toggle link 48, and the guide link 49, to move the plug valve 46 away from the second cannula extension member 64. This opens the second cannula 8 to receive air flowing from the first cannula upper passage 23 into the chamber 10. As the air flows through the second cannula 8 and the fenestration 40, it is presented to the trachea 3 above the cuff 35 and provides the air flow to the vocal cords that is necessary for speaking.

The pressure of the exhalation air is generally sufficient to maintain the check valve 44 in sealing engagement with the housing 9 to close off the first housing aperture 14. As the patient finishes exhaling, the respirator or normal inhalation activity sends another air pulse to move the check valve 44 from the second position back to the first position, thus beginning a repetition of the cycle.

It is noted that the flapper plate 54 hugs the outer walls of the housing 9 such that little, if any, incoming air passes by the flapper plate 54 until the flapper plate 54 passes the end of the curved housing end wall 55. It is at this point that the plug valve 46 has sealed, or is just about to seal, the second cannula extension member 64 so that little, if any, incoming air passes through the second cannula 8. It is preferred that none of the incoming air pass through the second cannula 8.

As illustrated, the first and second cannulae 6 and 8 have substantially equal effective cross-sectional areas. Because the second cannula 8 as illustrated is located within the first cannula 6, the open cross-sectional area of the first cannula 6 is substantially twice as great as the open cross-sectional area of the second cannula 8. This configuration yields equal effective cross-sectional areas for the first and second cannulae 6 and 8.

ALTERNATE EMBODIMENT OF THE INVENTION

An alternate embodiment of a tracheostomy device 101 is illustrated in FIGS. 10-13, which tracheostomy device 101 is similar in certain features to tracheostomy device 1 of the embodiment of FIGS. 1-9. Numerals having similar last two digits are used with reference to the tracheostomy devices 1 and 101 for similar parts except that the numerals of the instant embodiment are preceeded by the prefix "1". Thus, a first or outer cannula 106 is analagous in certain respects to the first cannula 6 of the previous embodiment.

The tracheostomy device 101 further includes a second or inner cannula 108, a dual valve housing 109 and dual valve means 112. The housing 109 defines a chamber 110 and a first housing aperture 114, which is adapted to receive a connector 115 from a source of air (not shown). A second housing aperture 117 opens into the outer cannula 106.

The outer cannula 106 has a first end 126 and a second end 127. The outer cannula first end 126 engages the housing 109 near the second housing aperture 117.

Inflatable sealing means are included, such as a sealing cuff 135 which is substantially similar to the sealing cuff 35. Appropriate inflation means 134 inflate the sealing cuff 135, as is well known in the art.

The inner cannula 108 has a first end 136 and a second end 137. The inner cannula 108 slides within the outer cannula 106.

The dual valve means 112 includes the inner cannula second end 137, a spring and bellows arrangement 181 and plate 184. The inner cannula second end 137 operates as a valve relative to a fenestration 140 through the outer cannula 106.

The spring and bellows arrangement 181 includes a wire spring 182 and a bellows 183. The inner cannula first end 126 includes a flange 185 extending circumferentially therefrom. A free disc 186 is situated between the outer cannula first end 126 and the housing 109. The bellows 183 is foldable and attached at a first end 188 thereof to the flange 185. A second end 189 of the bellows 183 is attached to the free disc 186.

As seen in FIGS. 11 and 12, the free disc 186 limits movement of the bellows second end 189 due to the physical arrangement of the housing 109 and outer cannula first end 126. As illustrated, the outer cannula first end 126 is slightly larger than the housing 109 and forms a recess 190 therebetween, which receives and holds the free disc 186.

The spring 182 is retained between the free disc 186 and the flange 185. The spring 182 and bellows 183 tend to bias away from the free disc 186, so as to slide the inner cannula 108 toward plate 184.

The inner cannula first end 136 has a plurality of orifices 191 therethrough for providing air communication from the area of the chamber 110 between the bellows 183 to the inner cannula 108.

The plate 184, as seen in FIG. 14, is integral with the housing 109 and has a plurality of passages 192 therethrough for providing air communication from the air source to the inner cannula 108. A cylindrical wall 194 extends from the plate 184 and is slidingly received in the inner cannula 108 to provide a seal, as seen in FIG. 12.

The housing 109 is removable, as for cleaning, and is connected to the cannula 106 by a cam lock (not shown). The outer cannula second end 127 receives the air connector 115 when the housing 109 is removed. The tracheostomy device 101 also includes means to provide access for suctioning and the like.

In use, the elements of the valve means 112 are adapted to respond to very low pressure differentials, such as are present when a person respirates.

FIG. 11 illustrates a first position of the valve means whereat air is flowing from the air source through the orifices 192 into the chamber 110. The air acts against the flange 185 and bellows 183, compressing the spring and bellows arrangement 181. The air then flows into the inner cannula 108 and through the outer cannula second end 127 into the patient's trachea for presentation to the lungs. The inner cannula second end 137 covers the fenestration 140, thereby preventing air from flowing from the fenestration 140 into the patient's trachea above the cuff.

A second position of the valve means 112 is shown in FIG. 12 and results from natural expansion of the spring and bellows arrangement 181. The spring and bellows arrangement 181 is very responsive to the low pressures involved during breathing.

The low resistance to movement of the spring and bellows arrangement 181 is a result of the mechanical advantage due to the relatively large surface area of the bellows 183 which is acted upon by the incoming breath. Thus, both embodiments of the invention utilize large mechanical advantages in their operation.

As the spring and bellows arrangement 182 expands, the inner cannula 108 slides along the outer cannula 106 until the inner cannula flange 185 and bellows first end 188 contact the housing 109, and the cylindrical wall 194 is surrounded by the inner cannula 108. When this contact is made, a seal is produced between the flange 185, diaphragm first end 188 and the housing 109, preventing air from flowing to or from the air source.

As the inner cannula 108 slides along the outer cannula 106, the inner cannula second end 137 passes by the fenestration 140, opening same. The exhalation air then passes through the fenestration 140 into the patient's trachea above the cuff 135, providing the air flow to the vocal cords that is necessary for speaking.

It is to be understood that while certain forms of the present invention have been illustrated and described herein, it is not to be limited to the specific forms or arrangement of parts described and shown.

What is claimed and desired to be secured by Letters Patent is as follows:

1. A tracheostomy device for insertion into a trachea and allowing a human patient to speak during a ventilation process; said device comprising:
    (a) an outer cannula having a first end and a second end; said outer cannula having a fenestration therethrough; said fenestration adapted to be located within a patient's trachea;
    (b) sealing means for forming a seal with a wall of the trachea and surrounding a portion of said outer cannula second end;
    (c) an inner cannula slidably received in said outer cannula and having a first end and a second end; said inner cannula having an orifice therethrough near said first end thereof;
    (d) a housing defining a chamber connected to said outer cannula second end; said housing chamber including means adapted to be in flow communication with an air source; and
    (e) dual valve means responsive to a patient's inhalation and exhalation process so as to selectively permit and inhibit flow of air from said air source while respectively inhibiting and permitting flow of air through said outer cannula fenestration 2. A tracheostomy device for insertion into a trachea and allowing a human patient to speak during a ventilation process; said device comprising:

(a) an outer cannula having a first end and a second end; said outer cannula having a fenestration therethrough; said fenestration adapted to be located within a patient's trachea;

(b) sealing means for forming a seal with a wall of the trachea and surrounding a portion of said outer cannula second end;

(c) an inner cannula slidably received in said outer cannula and having a first end and a second end; said inner cannula having an orifice therethrough near said first end thereof;

(d) a housing defining a chamber connected to said outer cannula second end; said housing chamber including means adapted to be in flow communication with an air source; and (e) spring and bellows means connected to said housing and said inner cannula and adapted to bias said inner cannula toward said air source, whereby said inner cannula second end is slidable away from a covering position over said outer cannula fenestration to inhibit flow of air from said air source and permit flow of air through said outer cannula fenestration; and said spring and bellows means adapted to contract in response to a patient's inhalation breath, whereby said inner cannula is slidable away from said air source and said inner cannula second end is slidable into a covering position over said outer cannula fenestration.

* * * * *